(12) United States Patent
Zivy et al.

(10) Patent No.: US 7,154,025 B2
(45) Date of Patent: Dec. 26, 2006

(54) METHOD FOR OBTAINING PLANTS EXHIBITING ENHANCED RESISTANCE TO WATER STRESS

(75) Inventors: Michel Zivy, Paris (FR); Pascual Perez, Chanonat (FR)

(73) Assignees: Biogemma, Paris (FR); Institut National de la Recherche Agronomique, Paris (FR); Association Generale des Producteurs de Mais Technique, Montardon (FR)

( * ) Notice: Subject to any disclaimer, the term of this patent is extended or adjusted under 35 U.S.C. 154(b) by 536 days.

(21) Appl. No.: 10/258,521

(22) PCT Filed: Apr. 24, 2001

(86) PCT No.: PCT/FR01/01252

§ 371 (c)(1),
(2), (4) Date: Mar. 14, 2003

(87) PCT Pub. No.: WO01/83756

PCT Pub. Date: Nov. 8, 2001

(65) Prior Publication Data

US 2004/0139505 A1    Jul. 15, 2004

(30) Foreign Application Priority Data

Apr. 28, 2000 (FR) .................................. 00 05534

(51) Int. Cl.
*C12N 15/82*    (2006.01)
*A01H 5/00*    (2006.01)

(52) U.S. Cl. ...................... 800/289; 435/468; 800/295

(58) Field of Classification Search ..................... None
See application file for complete search history.

(56) References Cited

U.S. PATENT DOCUMENTS 5,633,440 A * 5/1997 Dunsmuir et al. .......... 800/287

OTHER PUBLICATIONS

XP002157440, Frederique Riccardi et al., "Protein changes in response to progressive water deficit in maize.", Plant Physiology (Rockville), vol. 117, No. 4, Aug. 1998, pp. 1253-1263, ISSN:0032-0889.

XP002157441, Magdalena Rossi et al., "Asr gens belong to a gene family comprising at least three closely linked loci on chromosome 4 in tomato," Molecular & General Genetics, vol. 252, No. 4, 1996, pp. 489-492, ISSN: 0026-8925.

XP-002157442, Daniel Silhavy et al., "Isolation and characterization of a water-stress-inducible cDNA clone from Solanum chacoense," Plant Molecular Biology, vol. 27, No. 3, 1995, pp. 587-595, ISSN: 0167-4412.

XP002034436, Deping Xu et al., "Expression of a late embryogenesis abundant protein gene, HVA1, from barley confers tolerance to water deficit and salt stress in transgenic rice," Plant Physiology, US, American Society of Plant Physiologists, Rockville, MD., vol. 110, No. 1, 1996, pp. 249-257, ISSN: 0032-0889.

XP002157443, Database EMBL 'en ligne! Accession No. AW455731, Feb. 24, 2000, Walbot, V., "707090G04.x1 707—Mixed adult tissues from Walbot lab (SK) Zea mays cDNA, mRNA sequence."

XP002157444, Database EMBL 'en ligne! Accession No. AI677361, May 26, 1999, Walbot, V. "605054A04.x1 605—Endosperm cDNA library from Schmidt lab Zea mays cDNA, mRNA sequence."

XP002157445, Database EMBL 'en ligne! Accession No. AA979957, May 27, 1998, Wen T. J., "MEST4-B11.TW1412.Seq ISUM2 Zea mays cDNA clone MEST4-B11 5', mRNA sequence."

XP002157446, Database EMBL 'en ligne! Accession No. U09276, Oct. 3, 1994, Arredondo-Peter R. et al., "Zea mays ABA-and ripening-inducible-like protein mRNA, complete cds."

XP002157447, Database EMBL 'en ligne! Accession No. AI966921, Aug. 24, 1999, Walbot, V., "496019C12.x1 496—stressed shoot cDNA library from Wang/Bohnert lab ZEA mays cDNA, mRNA sequence."

XP002157448, Database EMBL 'en ligne! Accession No. AF039573, Jan. 17, 1998, Vaidyanathan R. et al., "Oryza sativa abscisic acid- and stress-inducible protein (Ars1) mRNA."

* cited by examiner

*Primary Examiner*—David H. Kruse
*Assistant Examiner*—Vinod Kumar
(74) *Attorney, Agent, or Firm*—Young & Thompson

(57) ABSTRACT

A method for obtaining a plant having a modified amount of ASR protein, providing it with enhanced resistance to water stress compared to a non-transformed plant, comprises: transforming at least a plant cell with a vector, containing an expression cassette including a nucleotide sequence coding for an ASR protein or inhibiting the expression of an ASR protein; culturing the resulting transformed cell so as to generate a plant containing in its genome the expression cassette.

8 Claims, 5 Drawing Sheets

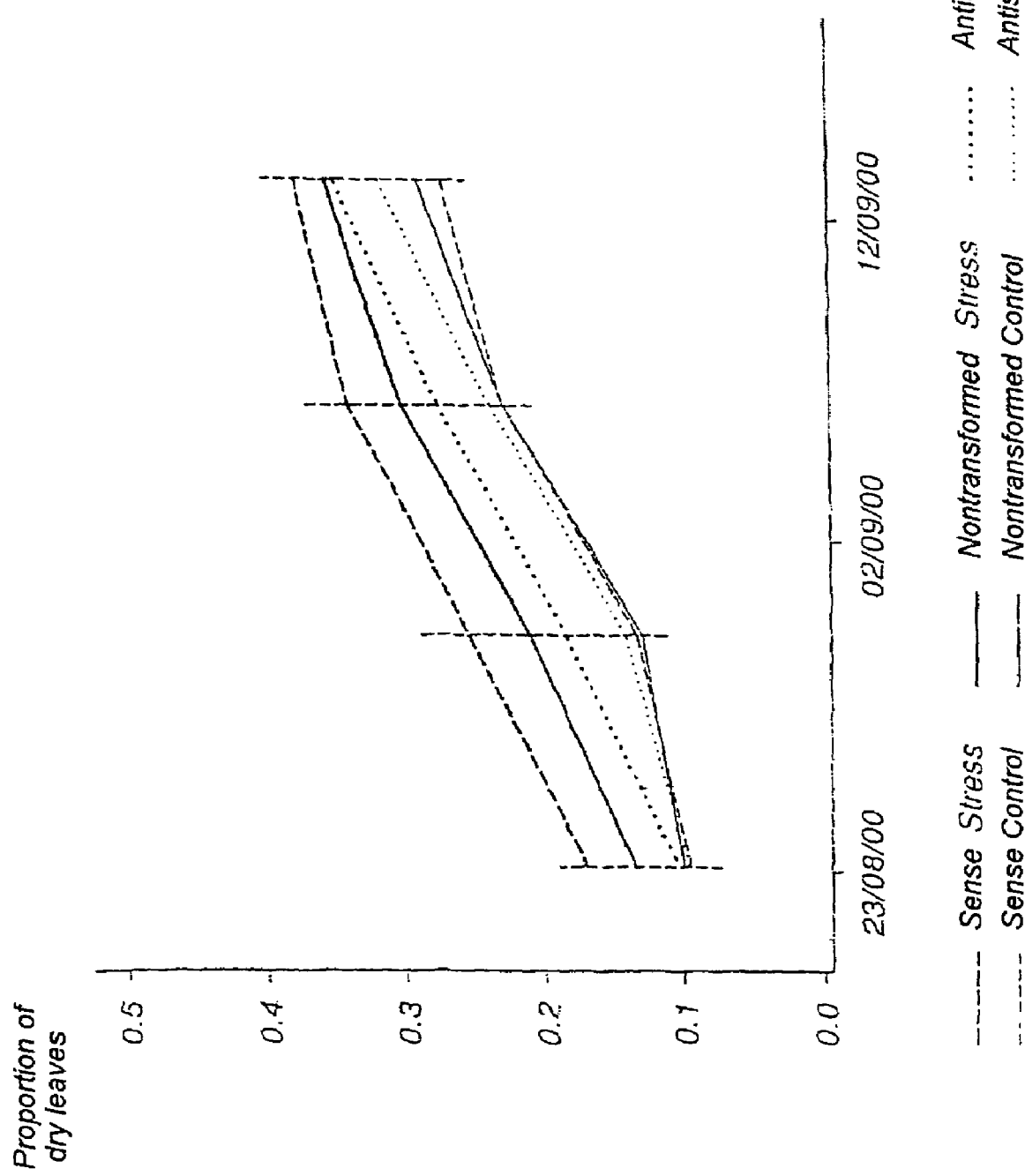

SEQUENCE LISTING

```
<160> NUMBER OF SEQ ID NOS: 7

<210> SEQ ID NO 1
<211> LENGTH: 777
<212> TYPE: DNA
<213> ORGANISM: Zea mays
<220> FEATURE:
<221> NAME/KEY: CDS
<222> LOCATION: (85)..(504)

<400> SEQUENCE: 1
tgtcgatcca attgtcactt gctctccctc caacaagcta attaaggccg gtcgtcatcc      60
ctcttctagc tcgttttatt atcc atg gcg gag gag aag cac cac cac cac       111
                           Met Ala Glu Glu Lys His His His His
                             1               5 cac ctg ttc cac cat aag aag gac gag gag cag gag gag cag ctc gcc       159
His Leu Phe His His Lys Lys Asp Glu Glu Gln Glu Glu Gln Leu Ala
 10                  15                  20                  25 ggc ggc ggg tac ggc gag tcc gcc gag tac acg gag gcc acg gtg acg       207
Gly Gly Gly Tyr Gly Glu Ser Ala Glu Tyr Thr Glu Ala Thr Val Thr
                 30                  35                  40 gag gtg gtg tcc acg ggc gag aac gag tac gac gag tac aag gag gag       255
Glu Val Val Ser Thr Gly Glu Asn Glu Tyr Asp Glu Tyr Lys Glu Glu
             45                  50                  55 aag cag cat aag cac aag cag cac ctc ggc gag gcc ggc gcc atc gcc       303
Lys Gln His Lys His Lys Gln His Leu Gly Glu Ala Gly Ala Ile Ala
         60                  65                  70 gcc ggc gcc ttc gca ctc tac gag aag cac gag gca aag aag gac ccg       351
Ala Gly Ala Phe Ala Leu Tyr Glu Lys His Glu Ala Lys Lys Asp Pro
 75                  80                  85 gag cac gcg cac cgc cac aag atc gag gag gag gtc gcg gcg gcg gcg       399
Glu His Ala His Arg His Lys Ile Glu Glu Glu Val Ala Ala Ala Ala
 90                  95                 100                 105 gcc gtc ggc tcc ggc ggc ttc gcc ttc cac gag cac cac gag aag aag       447
Ala Val Gly Ser Gly Gly Phe Ala Phe His Glu His His Glu Lys Lys
                110                 115                 120 aag gac cac aag gac gcc gag gag gcc ggc ggc gag aag aag cac cac       495
Lys Asp His Lys Asp Ala Glu Glu Ala Gly Gly Glu Lys Lys His His
            125                 130                 135 ttc ttc ggc tgattgatcc ctcccgtatc gtcgtccctc cccgtgtgct               544
Phe Phe Gly
        140 acgcgtgcgt gtgtgagagt gatatcgagc gcccgccgtg ttgtgcgcgc gtacgtatgt     604 atgcgctcgt gtgatgcacg aataagcgtg gctacgtaat ctatcgtatg tatacgtgtg     664 tgtatgcatg tgcttgtgta tgatcgtggt acgaggaccg aaaaaatgta tgcaactctg     724 atttacttac atgtttagtt gtttacgttt ctccaaaaaa aaaaaaaaaa aaa            777
```

<210> SEQ ID NO 2
<211> LENGTH: 140
<212> TYPE: PRT
<213> ORGANISM: Zea mays

<400> SEQUENCE: 2

Met Ala Glu Glu Lys His His His His Leu Phe His His Lys Lys
 1               5                  10                  15
Asp Glu Glu Gln Glu Glu Gln Leu Ala Gly Gly Gly Tyr Gly Glu Ser
                20                  25                  30
Ala Glu Tyr Thr Glu Ala Thr Val Thr Glu Val Val Ser Thr Gly Glu
            35                  40                  45
Asn Glu Tyr Asp Glu Tyr Lys Glu Glu Lys Gln His Lys His Lys Gln
        50                  55                  60
His Leu Gly Glu Ala Gly Ala Ile Ala Ala Gly Ala Phe Ala Leu Tyr
 65                 70                  75                  80
Glu Lys His Glu Ala Lys Lys Asp Pro Glu His Ala His Arg His Lys
                85                  90                  95
Ile Glu Glu Glu Val Ala Ala Ala Ala Val Gly Ser Gly Gly Phe
            100                 105                 110
Ala Phe His Glu His His Glu Lys Lys Lys Asp His Lys Asp Ala Glu
        115                 120                 125
Glu Ala Gly Gly Glu Lys Lys His His Phe Phe Gly
    130                 135                 140

<210> SEQ ID NO 3
<211> LENGTH: 892
<212> TYPE: DNA
<213> ORGANISM: Zea mays

<400> SEQUENCE: 3
tgtcgatcca attgtcactt gctctccctc caacaagcta attaaggccg gtcgtcatcc      60
ctcttctagc tcgttttatt atccatggcg gaggagaagc accaccacca ccacctgttc     120
caccataaga aggacgagga gcaggaggag cagctcgccg gcggcgggta cggcgagtcc     180
gccgagtaca cggaggccac ggtgacggag gtggtgtcca cgggcgagaa cgagtacgac     240
gagtacaagg aggagaagca gcataagcac aagcagcacc tcggcgaggc cggcgccatc     300
gccgccggcg ccttcgcact cgtacgtagt cctccgatcg atccgatcct ccttgagtag     360
tatatacata catgaacgcg ataacgaata atatattaat cgaacgaact gaatgatgat     420
cacggatcac ctcgtgtgac gtggacatgc acagtacgag aagcacgagg caaagaagga     480
cccgagcac gcgcaccgcc acaagatcga ggaggaggtc gcggcggcgg cggccgtcgg     540
ctccggcggc ttcgccttcc acgagcacca cgagaagaag aaggaccaca aggacgccga     600
ggaggccggc ggcgagaaga agcaccactt cttcggctga ttgatccctc ccgtatcgtc     660
gtccctcccc gtgtgctacg cgtgcgtgtg tgagagtgat atcgagcgcc gccgtgttg      720
tgcgcgcgta cgtatgtatg cgctcgtgtg atgcacgaat aagcgtggct acgtaatcta     780
tcgtatgtat acgtgtgtgt atgcatgtgc ttgtgtatga tcgtggtacg aggaccgaaa     840
aaatgtatgc aactctgatt tacttacatg tttagttgtt tacgtttctc ca             892

<210> SEQ ID NO 4
<211> LENGTH: 890
<212> TYPE: DNA
<213> ORGANISM: Zea mays

<400> SEQUENCE: 4

```
tgtcgatcca attgtcactt gctctccctc caacaagcta attaaggccg gtcatccctc      60
ttctagctcg tttcattatc catggcggag gagaagcacc accaccacca cctgttccac     120
cacaagaagg acgaggagca ggaggagcag ctcgccggcg gcgggtacgg cgagtccgcc     180
gagtacacgg aggccacggt gacggaggtg gtgtccacgg gcgagaacga gtacgacgag     240
tacaagaagg aggagaagca gcacaagcac aagcagcacc tcggcgaggc cggcgccatc     300
gccgccggcg ccttcgcact cgtacgtagt cctccgatcg atccgatcct ccttgagtag     360
tatatacata catgaacgcg ataacgaata atatattaat cgaacgaact gaatgatgat     420
cacggatcac ctcgtgtgac gtggacatgc acagtacgag aagcacgagg caaagaagga     480
cccggagcac gcgcaccgcc acaagatcga ggaggaggtc gcggcggcgg cggccgtcgg     540
ctccggcggc ttcgccttcc acgagcacca cgagaagaag aaggaccaca aggacgccga     600
ggaggccggc ggcgagaaga agcaccactt cttcggctga ttgatccctc ccgtatcgtc     660
gtccctcccc gtgtactacg cgtgcgtgtg tgagagtgat atcgagcgcc cgccgtgttg     720
tgcgcgcgta cgtatgtatg cgctcgtgtg atgcacgaat aagcgtggct acgtaatcta     780
tcgtatgtat acgtgtgtgt atgcatgtgc ttgtgtatga tcgtggtacg aggaccgaaa     840
aaatgtatgc aactctgatt tacttacatg tttagttgtt tacgtttctc                890
```

<210> SEQ ID NO 5
<211> LENGTH: 814
<212> TYPE: DNA
<213> ORGANISM: Zea mays
<220> FEATURE:
<221> NAME/KEY: modified_base
<222> LOCATION: (793)
<223> OTHER INFORMATION: a, t, c, g, other or unknown

<400> SEQUENCE: 5

```
gctaattaag gccggtcgtc atccctcttc tagctcgttt tattatccat ggcggaggag      60
aagcaccacc accaccacct gttccaccat aagaaggacg aggagcagga ggagcagctc     120
gccggcggcg ggtacggcga gtccgccgag tacacggagg ccacggtgac ggaggtggtg     180
tccacgggcg agaacgagta cgacgagtac aagaaggagg agaagcagca agcacaag      240
cagcacctcg gcgaggccgg cgccatcgcc gccggcgcct tcgcactcgt acgtagtcct     300
ccgatcgatc cgatcctcct tgagtagtat atacatacat gaacgcgata acgaataata     360
tattaatcga acgaactgaa tgatgatcac ggatcacctc gtgtgacgtg gacatgcaca     420
gtacgagaag cacgaggcaa agaaggaccc ggagcacgcg caccgccaca agatcgagga     480
ggaggtcgcg gcggcggcgg ccgtcggctc cggcggcttc gccttccacg agcaccacga     540
gaagaagaag gaccacaagg acgccgagga ggccggcggc gagaagaagc accacttctt     600
cggctgattg atcctcccgt atcgtcgtcc ctccccgtgt gctacgcgtg cgtgtgtgag     660
actgatatcg agcgcccgcc gtgttgtgcg cgcgtacgta tgtatgcgct cgtgtgatgc     720
acgaataagc gtggctacgt aatctatcgt atgtatacgt gtgtgtatgc atgtgcttgt     780
gtatgatcgt ggnacgagga ccgaaaaaat gtat                                  814
```

<210> SEQ ID NO 6
<211> LENGTH: 20
<212> TYPE: DNA
<213> ORGANISM: Zea mays

```
<400> SEQUENCE: 6
tgtcgatcca attgtcactt                                               20

<210> SEQ ID NO 7
<211> LENGTH: 20
<212> TYPE: DNA
<213> ORGANISM: Zea mays

<400> SEQUENCE: 7
tggagaaacg taaacaacta                                               20
```

METHOD FOR OBTAINING PLANTS EXHIBITING ENHANCED RESISTANCE TO WATER STRESS

The present invention relates to a method for obtaining plants exhibiting enhanced resistance to water stress.

In temperate regions, periods of low rainfall, which vary in intensity and are unpredictable, are the cause of a notable decrease in productivity in crop plants. The water deficit can severely affect plant growth and reproduction. Various strategies making use of physiological mechanisms (decrease in growth of aerial parts, closure of stomata) and/or cellular mechanisms (osmotic adjustment) may enable them to evade this water stress, or at the very least to tolerate it. These mechanisms, which are at least partly controlled by ABA (abscisic acid), a phytohormone the concentration of which increases in plants subjected to water stress (Zeevaart and Creelman, 1988), involve many proteins with different putative functions: proteins of the membrane channel type, or proteins expressed in response to damage caused to the cell (proteases, protease inhibitors), or else proteins whose functions are not directly related to stress but which are expressed at higher levels under conditions of water or salinity stress (enzymes of glycolysis, of methionine synthesis). The plant's response depends, moreover, on environmental (type of restraint, intensity, duration) and genetic (species and genotype) parameters, making it difficult to determine the role of these proteins in the mechanisms of tolerance to drought.

There is therefore a real need to demonstrate the function of candidate genes in the mechanisms of tolerance to water stress, in order to use them in transgenesis aimed at obtaining plants exhibiting better tolerance to water stress. This is particularly important for field crop species, such as maize, for example, which attains a level of maximum sensitivity to drought 15 days before and 15 days after flowering of the plant (July–August in Europe), a period during which the plant would absorb 45% of its total needs.

A first study carried out by Riccardi et al. (1998) on a maize line designated Io (Iodent) has demonstrated about twenty proteins, the expression of which is significantly increased in response to water stress, and for which putative functions have been proposed.

One of these proteins, demonstrated in the Io line used by Riccardi et al. (1998) but not in the F2 line, exhibits homologies with a tomato protein which is induced by ABA, water stress and ripening of the fruit, ASR1 (ABA-water stress-ripening-induced protein), but the function of which is still unknown (Iusem et al., 1993). Other genes showing homologies with tomato ASR have been identified, in particular in potato (Silhavy et al., 1995), lemon (Canel et al., 1995) and rice (Thomas et al., 1999), but no function has been clearly demonstrated for the proteins encoded by these genes. A QTL (Quantitative Trait loci) study has made it possible to map the Asr1 gene in a region containing both the locus controlling the amount of ASR1 and QTLs for foliar senescence and protandry (De Vienne et al., 1999).

The authors of the present invention have now demonstrated the role of a recombinant ASR protein in the direct response of a plant to water stress, in order to use transgenesis. Specifically, they have succeeded in developing a method for obtaining a plant having a modified amount of ASR protein, conferring on it better resistance to water stress compared to a nontransformed plant.

A subject of the invention is therefore a method for obtaining a plant containing a modified amount of ASR protein, conferring on it better resistance to water stress compared to a nontransformed plant, comprising the steps consisting in:

transforming at least one plant cell with a vector containing an expression cassette comprising a nucleotide sequence encoding an ASR protein or blocking the expression of an ASR protein;

culturing the cell thus transformed so as to generate a plant containing, in its genome, said expression cassette.

The term "ASR protein" is intended to mean a protein expressed naturally by a plant in response to water stress, having an amino acid sequence identical or homologous to the maize sequence SEQ ID No 2.

The term "homologous sequence" is intended to mean preferably a sequence exhibiting at least 50%, preferably 70%, similarity with the sequence SEQ ID No 2.

For the purpose of the invention, included in the definition of "ASR protein" are all the ASR proteins of various plants, such as, for example, that of rice, and also the proteins which are modified, for example by addition, deletion and/or substitution (preferably conservative substitution) of a small number of amino acids.

Also included in the definition of "ASR protein" are the polypeptides encoded by all or part of the sequence SEQ ID No 1, No 3, No 4 or No 5, or any homologous sequence, it being understood that these polypeptides conserve the property of resistance to water stress.

The nucleic acid sequence encoding an ASR protein may more particularly be a sequence from a cereal, in particular a sequence from maize.

Said sequence may advantageously be a cDNA sequence specific for the state of water stress, isolated from a maize line by differential hybridization. Such a sequence is given in the attached sequence listing, and designated SEQ ID No 1. It is also possible to use a genomic DNA sequence encoding a maize ASR protein, as defined by one of the sequences SEQ ID No 3, SEQ ID No 4 and SEQ ID No 5, or a sequence homologous thereto, provided that it is expressed in modified amounts compared to the amount usually produced by a nontransformed plant.

In the attached sequence listing,

SEQ ID No 3 is a genomic DNA sequence isolated from a maize line which strongly expresses the ASR protein, SEQ ID No 4 is a genomic DNA sequence isolated from a control maize line A188, and SEQ ID No 5 is a genomic DNA sequence isolated from an $F_2$ maize line.

Said sequence may in particular encode the amino acid sequence SEQ ID No 2 of the maize ASR protein, or a variant thereof, for example a variant having the sequence SEQ ID No 2 with an insertion of a lysine residue between amino acids 55 and 56 of SEQ ID No 2.

It is also possible to use nucleotide sequences encoding ASRs from other plants, such as, for example, those cited above.

The nucleic acid encoding an ASR protein is inserted into a nucleic acid construct, called expression cassette, and is functionally linked to elements which allow the expression thereof and, optionally, the regulation thereof.

Among these elements, mention may be made of promoters, activators and terminators of transcription.

Use may preferentially be made of a constitutive promoter, such as the rice actin promoter, followed by the rice actin intron (RAP-RAI) contained in the plasmid pAct1-F4 (Mc Elroy et al., 1991) or the 35S promoter (Kay et al., 1987), or a tissue-specific promoter. By way of example, mention may be made of the wheat HMWG promoter or the radish cruciferin gene promoter, PCRU, which both allow expression of the protein of interest in the seeds (Anderson O. D. et al., 1989; Depigny-This et al., 1992). Use may advantageously be made of promoter sequences which induce expression under water conditions (Kasuga et al., 1999). Among the terminators which can be used in the constructs of the invention, mention may in particular be made of the 3' end of the *Agrobacterium tumefaciens* nopaline synthase gene (Depicker et al., 1982). Mention may also be made of the 35S polyA terminator of the cauliflower mosaic virus (CaMV), described in the article by Franck et al. (1980).

The expression of the ASR protein can also be regulated by using sequences such as peptide addressing signals (chloroplast addressing signals, vacuolar addressing signals, addressing signals for endoplasmic retention, etc.), or such as intron sequences, enhancer sequences or leader sequences.

In the present invention, the sequence of interest may be a nucleotide sequence encoding an ASR protein, said sequence being placed in the sense direction, or a nucleotide sequence blocking the expression of an ASR protein. This nucleotide sequence blocking the expression of the ASR protein is preferentially a sequence encoding all or part of the ASR protein, said sequence being placed in the antisense direction. When the sequence encoding an ASR protein is placed in the sense direction, a transformed plant is obtained which exhibits an increase in the ASR protein compared to a nontransformed plant. This plant has the advantage of withstanding water stress more effectively than a nontransformed plant. When the sequence is placed in the antisense direction, a transformed plant is obtained which also exhibits a modification of resistance to water stress. Without adhering in any way to a precise mechanism of action, this observation might be explained by the plant activating an alternative pathway of resistance to water stress, in response to inhibition of the ASR by the antisense sequences.

The expression cassette is inserted into a nucleotide vector, such as a plasmid, which may also comprise a marker gene, for example a gene making it possible to select between a transformed plant and a plant which does not contain the transfected foreign DNA. As marker gene, mention may be made of a gene which confers resistance to an antibiotic, for example to hygromycin (Herrera-Estrella et al., 1983) or resistance to a herbicide such as the sulfonamide asulam (WO 98/49316).

This vector or any sequence encoding an ASR protein, such as the sequences SEQ ID No 1, SEQ ID No 3, SEQ ID No 4 and SEQ ID No 5, or sequences homologous to the latter, can be used to transform plant cells according to techniques commonly known to those skilled in the art, in order to obtain plants exhibiting enhanced resistance to water stress.

According to one embodiment of the method of the invention, the plant cells are transformed with a vector as defined above, transferred into a cellular host capable of infecting said plant cells by allowing integration into the genome of the latter of the nucleotide sequences of interest initially contained in the genome of the abovementioned vector. Advantageously, the cellular host used is a bacterial strain, such as *Agrobacterium tumefaciens*, in particular according to the method described in the article by An et al. (1986), or else *Agrobacterium rhizogenes*, in particular according to the method described in the article by Guerche et al. (1987).

For example, the plant cells can be transformed by transferring the T region of the *Agrobacterium tumefaciens* extrachromasomal, circular, tumor-indicating Ti plasmid, using a binary system (Watson et al., 1994). To do this, two vectors are constructed. In one of these vectors, the T region has been removed by deletion, with the exception of the left and right borders, a marker gene being inserted between them so as to allow selection in the plant cells. The other partner of the binary system is a helper Ti plasmid, which is a modified plasmid which no longer has a T region but which still contains the vir virulence genes required for transformation of the plant cell.

According to a preferred mode, use may be made of the method described by Ishida et al. (1996), for the transformation of monocotyledons.

Other embodiments of the method of the invention may also be mentioned, in particular methods of direct gene transfer into plant cells, such as direct microinjection into plant embryoids (Neuhaus et al., 1987), infiltration under vacuum (Bechtold et al., 1993) or electroporation (Chupeau et al., 1989), or else direct precipitation using PEG (Schocher et al., 1986) or bombardment with particles covered with the plasmid DNA of interest, using a particle gun (M. Fromm et al., 1990).

According to another protocol, the transformation is carried out according to the method described by Finer et al. (1992), using a tungsten or gold particle gun.

The subject of the invention is also a host cell transformed with the nucleic acid sequences described above, and also a plant or part of a plant, in particular fruit, seed, grain, pollen, leaf or tuber, which can be obtained using one of the methods set out above.

They may, for example, be field crop plants (wheat, rapeseed, sunflower, peas, soybean, barley, in particular maize, etc.) or vegetables and flowers.

The hybrid transgenic plants, obtained by crossing at least one plant according to the invention with another, are also part of the invention.

The invention in particular relates to a plant exhibiting an increase in expression of the ASR protein compared to a nontransformed plant, for example a 2- to 3-fold increase. This increase in expression of the ASR protein confers enhanced resistance to water stress on the transformed plants.

The resistance to water stress of the transformed plants according to the invention, compared to the control plants, can be assessed using various morphological, physiological and/or biochemical measuring methods, for particular irrigation conditions. By way of example, the tolerance to stress can be measured by phenotypic observation (i) of foliar senescence, by morphological measurements and by assaying the chlorophyll in the foliar disks, (ii) of the protandry or date of flowering of the male and female plants, (iii) of the growth of the plant, by measuring the final length and width of the leaves and also the final height of the plant, and by studying the rolling up of the leaves, or else (iv) of the yield of grain, of the weight of a thousand grains and of the number of ears per plant.

The stress experienced by the plants can also be evaluated by measuring the ABA content (method of Quarrie et al., 1988) or by measuring the water potential, or else, where appropriate, by monitoring expression of the protein by two-dimensional electrophoresis using a leaf sample.

The plants obtained according to the invention can also be used in allele complementation experiments in order to validate the function of the inserted gene. Use of the transformants in backcross experiments makes it possible to introduce only the gene inserted in the parental genetic background, without other sequences which might influence the phenotype of the recombinant with regard to tolerance to drought.

Preferably, the inserted gene is coupled with a selectable marker gene, which facilitates the monitoring of the backcrosses and, consequently, the monitoring of the insertion of the gene of interest into the line in which it is desired to validate the effect.

The principle consists in crossing the transformant with the parental line not possessing the favorable allele of the gene of interest, and comparing the phenotypes of the recombinant line with the parental lines. It is also possible to use transformants containing the genomic sequences in these complementation experiments. This complementation assay makes it possible to verify in particular that overexpression of the cDNA in the sense direction complements the effect of the weak (or null) allele.

Thus, it is, for example, possible to verify that the ASR1 gene is the gene responsible for the QTL and PQL (protein quantitative loci), found at this genetic position on chromosome 10 in maize. Since the amount of this protein varies between different lines, stronger expressions; or even expressions of more favorable alleles, can be detected and exploited for improving plants. Plants exhibiting favorable alleles can be detected by immunoassays with antibodies specific for the ASR1 protein (ELISA assay, Western blotting, etc.).

The use of a nucleic acid encoding an ASR, of a fragment of this nucleic acid, as a probe or primer for PCR-type amplification, in order to select transformed plants exhibiting better resistance to water stress, also falls within the context of the invention.

The nucleic acid sequences encoding an ASR, such as those designated SEQ ID No 1, SEQ ID No 3, SEQ ID No 4 and SEQ ID No 5, and also any oligonucleotide obtained from one of these sequences, can thus be used as probes in marker-assisted selection programs, for example for following the introgression of the gene encoding the maize ASR protein into a plant. For this, at least one of these probes is labeled, for example with a radioactive isotope, and then brought into contact with genomic DNA from the plant, predigested with restriction enzymes, under conditions which allow specific hydration of the labeled probe to the DNA in question. Other techniques using for example PCR may also be used to carry out genotyping.

The following figures and examples illustrate the invention without limiting the scope thereof.

LEGEND TO THE FIGURES

FIG. 5 represents kinetics of the effect, for all the "sense", "nontransformed" and "antisense" events, possibly placed under conditions of water stress, on foliar senescence.

EXAMPLES

Example 1

Figure 1:
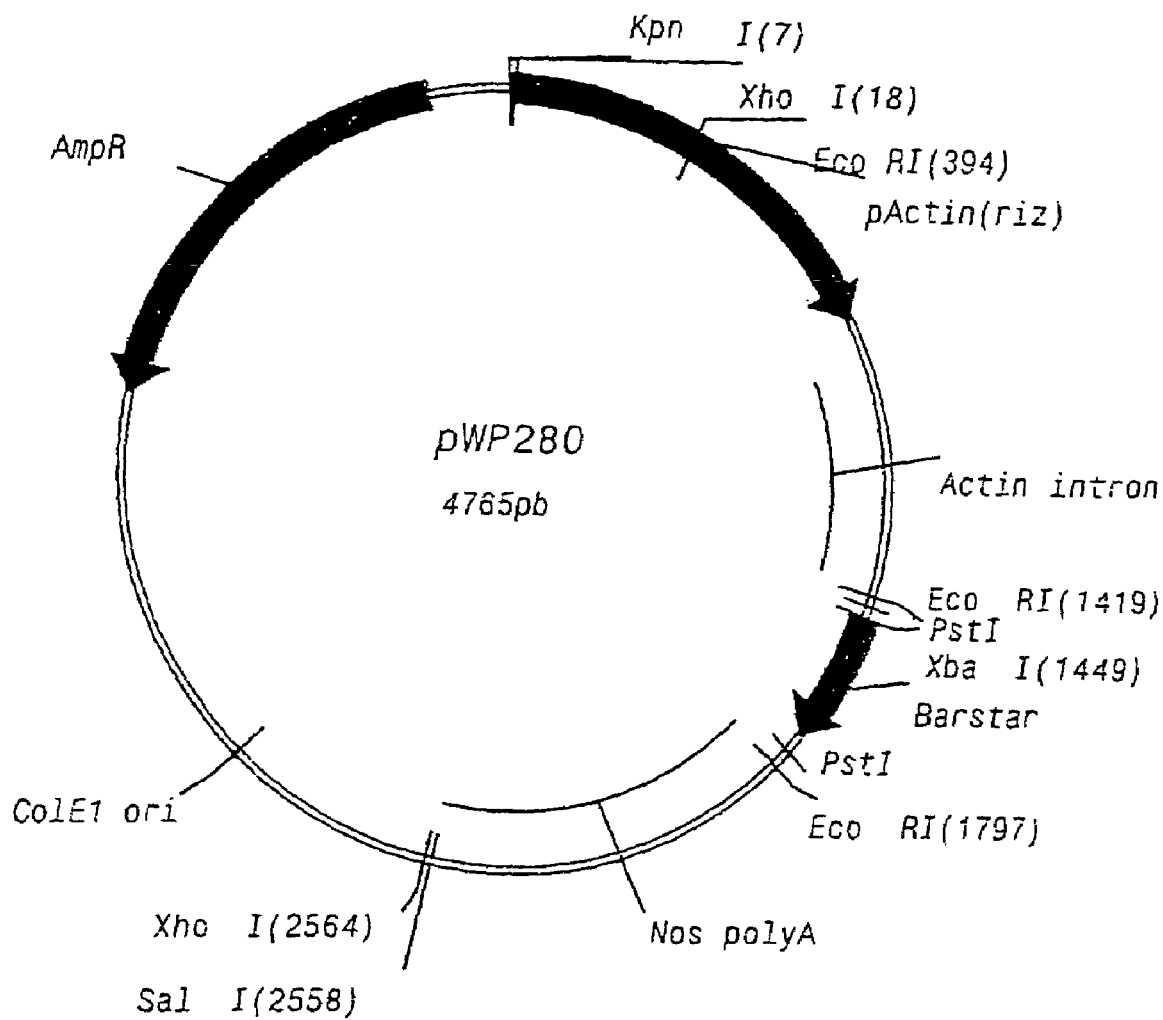
FIG. 1 represents a restriction map of the plasmid pWP 280 containing the promoter pActin intron-barnase-Nos PolyA.

Obtaining and Cloning the cDNA of ZmAsr1 from a Maize Line Which Strongly Expresses the ASR Protein a) Culture Conditions and Taking of Samples for the Plants Having Been Used to Isolate the cDNA The authors of the invention cloned the ZmAsr1 cDNA from Io maize lines (Riccardi et al., 1998) or from maize lines selected according to the same criteria as Io.

The maize plants are grown in perlite under controlled conditions in a culturing chamber (illumination: 450 mmol $m^{-2}$ $s^{-1}$, photoperiod: 16 h, day/night temperature: 25° C./20° C., relative humidity 60%), watered with a nutrient solution. When the plants have reached the "5 leaf" stage (5th emerged leaf), the watering is either stopped, for the plants under conditions of water stress, or it is continued, for the control plants. Ten days later, samples are taken from the ensheathed part of the blade of the 7th leaf.

b) Isolating the cDNAs Specific for the State of Water Stress by Differential Hybridization A cDNA library is prepared from mRNA from the leaves of stressed plants using the Lambda ZapII cDNA synthesis/ Gigapack GoldI cloning kit (Stratagene, La Jolla, USA), according to the manufacturer's intructions.

The mRNAs prepared from the leaves of stressed plants and of control plants are transcribed into radiolabeled cDNA using 100 μCi of $^{32}$P-dATP and hexanucleotides serving as random primers (Sambrook et al., 1989). The single-stranded cDNAs, originating either from the stressed plant or from the control plant, are hybridized, in the same proportion, on the cDNA clones of the library. The hybridization temperature in the phosphate buffer/SDS/EDTA system (Church and Gilbert, 1984) is 68° C. and the final washes are carried out with solutions containing 0.1×SSC, 0.05% (weight/volume) SDS.

The labeled clones are recovered by in vivo excision of the phagemid according to the Stratagene protocol using *E. coli* SOLR and the "Exassist" helper phage. The DNA of these clones is sequenced and compared to nucleic acid sequence libraries (BLAST) according to the method described in Altschul et al. (1990). One of these clones exhibits strong homology with tomato Asr1 and is named ZmAsr1 for Zea maize Asr1.

Example 2

ZmASR1 Genomic Sequences

The primers cASR1-1F (5'-TGTCGATCCAATTGT-CACTT-3')=SEQ ID No 6 and cASR1-740R (5'-TG-GAGAAACGTAAACAACTA-3')=SEQ ID No 7, defined at the two ends of the cDNA sequence of the ASR1 protein, are used in PCR amplification on maize line total DNA. The PCR reactions are carried out according to conventional techniques.

The PCR products are analyzed by electrophoresis: a band at 900 bp is recovered in order to extract the DNA therefrom and clone it according to conventional techniques. After verification of their size, the inserts are extracted and sequenced.

Example 3

Construction of Chimeric Genes for the Constitutive Expression of the ASR1 Protein or Else of an Antisense Leading to Inhibition Thereof.

First, 2 basic plasmid vectors are constructed, pBIOS 306 and pBIOS 307, containing the actin promoter-actin intron (pAct), the cDNA of the Asr1 gene, respectively in the sense and antisense direction, and the nopaline synthase terminator (terNos) which introduces a polyadenylation signal which is functional in many plant species.

Intermediate vectors are then produced for homologous recombination with the Japan Tobacco vector pSB1 (EP 672 752) in *Agrobacterium tumefaciens* strain LBA 4404 (Hoekema et al., 1983).

The transfer followed by the expression of the genes (gene for selection and gene of interest) into maize is based on the natural properties of *Agrobacterium tumefaciens* (Zambrisky et al., 1989) and on the superbinary plasmid strategy (Hiei et al., 1994 and Ishida et al., 1996).

The restriction enzymes used for the cloning are provided by New England Biolabs (New England Biolabs, UK). The enzymatic reactions are carried out by following the protocols described, by Sambrook et al., in the molecular cloning manual (Molecular Cloning: A Laboratory Manual, 1989, Cold Spring Harbor Laboratory Press, Cold Spring Harbor, N.Y.

a) Construction of the Basic Plasmid Vectors for the Constitutive Expression of the Asr1 Gene and of its Antisense The molecular constructs for the constitutive expression of the Asr1 gene in the sense and antisense direction were prepared as described below:

cloning of the 795 bp I/XhoI fragment (Asr1 cDNA=SEQ ID No 1) into the EcoRV-restricted vector pBIOS 298.

The vector pBIOS 298 contains the actin promoter-actin intron (pAct) (Mc Elroy et al., 1991) and the Nos terminator. This vector was generated by deletion of the 366 bp PstI fragment (Barstar gene) of the vector pWP 280, containing the pActin-intron~Barstar~Nos polyA cassette (FIG. 1).

This nonoriented cloning makes it possible to obtain 2 new vectors:

the vector pBIOS 306 carrying the gene pAct-ZmAsr1 sense-terNos the vector pBIOS 307 carrying the gene pAct-ZmAsr1 antisense-terNos.

The orientation of the cDNA relative to the actin promoter was determined by simple enzymatic restriction with EagI and double enzymatic restriction with Hind III-EcoRV.

b) Construction of the Intermediate Vectors for Homologous Recombination with pSB1 (Obtaining Superbinary Plasmids)

The vectors used for the homologous recombination in *Agrobacterium tumefaciens* are derived from the vector pBIOS 273.

Construction of the Plasmid pBIOS 273

The basic vector for the homologous recombination is the vector PBIOS 273. This vector was generated in 2 steps:

Cloning of the BspDI/XhoI fragment (pAct-Bar-terNos) of the vector pDM 302 (Cao et al., 1992) into the SmaI and BspDI sites of the vector pSB12 (Japan Tobacco). The vector resulting from this cloning is called pBIOS 272.

Deletion of the XhoI site at position 3363 of the vector pBIOS 272 by partial digestion with XhoI and the action of DNA Polymerase I large (Klenow) fragment. The vector obtained, which has a unique XhoI site, is named pBIOS 273.

Generation of the Intermediate Recombination Vectors Containing the Asr1 cDNA in the Sense or Antisense Direction These constructs were generated from the vector pBIOS 274, derived from the vector pBIOS 273 by cloning the XhoI fragment (ProA9-Barnase-terCaMV) of the vector pWP 128 (Paul et al., 1992) into the XhoI-restricted vector pBIOS 273.

The intermediate vectors pBIOS 308 and pBIOS 309 were obtained by cloning the 2970 bp SalI/XhoI fragments of the Vectors pBIOS 306 and pBIOS 307 into the BspDI/XhoI sites of the vector PBIOS 274.

Figure 2:
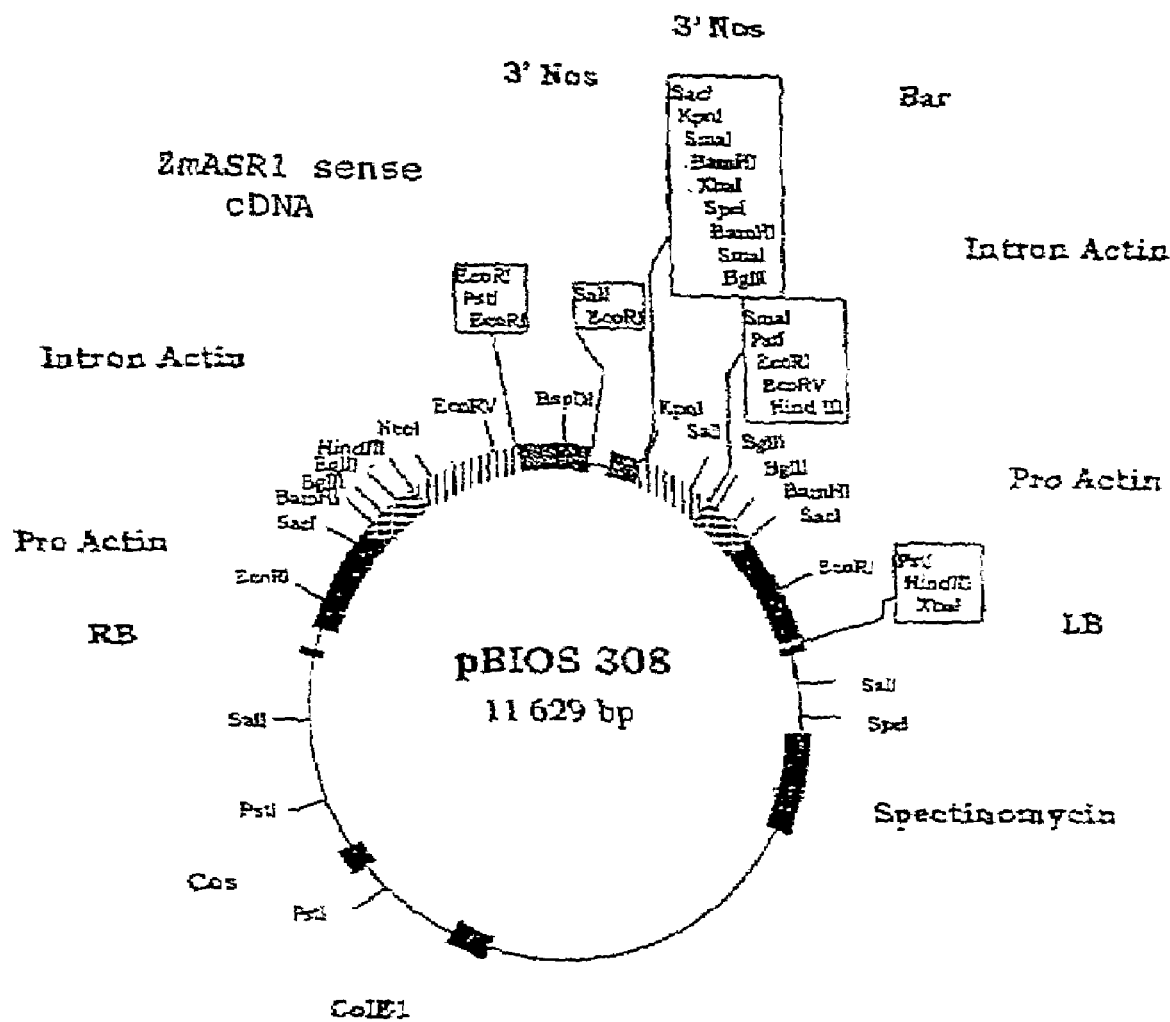
FIG. 2 represents a restriction map of the intermediate vector pBIOS 308 containing ZmASR1 cDNA in the sense direction.
Figure 3:
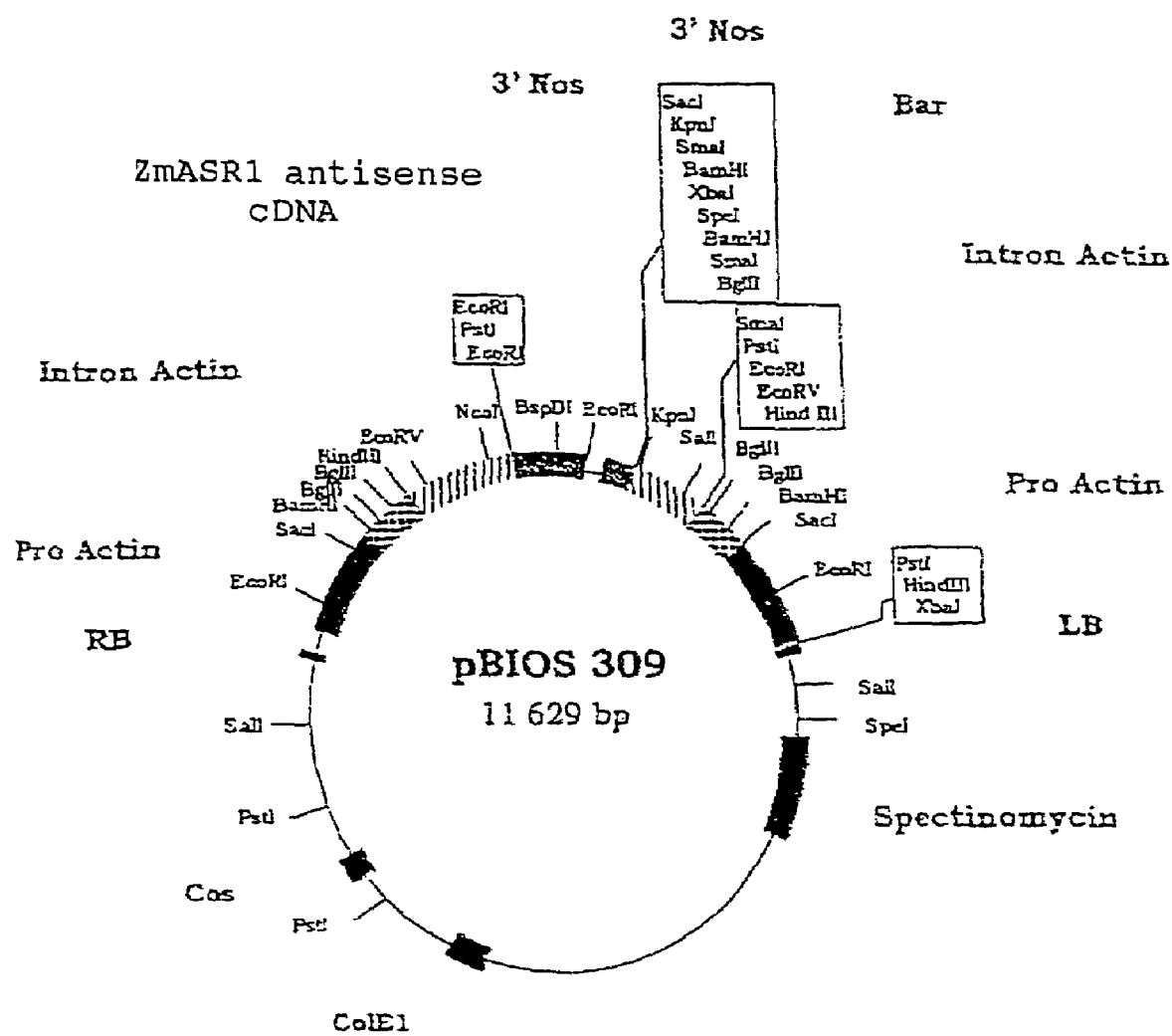
FIG. 3 represents a restriction map of the intermediate vector PBIOS 309 containing ZMASR1 cDNA in the antisense direction.

This cloning thus makes it possible to substitute the pA9-Barnase-terCaMV gene of the vector pBIOS 274 with the pAct-ZmAsr1 sense-terNos gene, the resulting vector being called pBIOS 308 (FIG. 2), or with the pAct-ZmAsr1 antisense-terNos gene, the resulting vector being called pBIOS 309 (FIG. 3).

c) Construction of the Superbinary Transformation Vectors for Expression of the Asr1 Gene and of Its Antisense in *Agrobacterium tumefaciens* and in Maize Plants Construction of the Superbinary Vectors The vectors used for the transformation of maize are derived from homologous recombination of the plasmids pBIOS 308 and pBIOS 309 with the vector pSB1 (EP 672 752). The vector pSB1 contains the virB and virG genes of the Ti plasmid pTiBo542 present in the *Agrobacterium tumefaciens* strain A281 (ATCC 37349), the tetracyclin resistance gene, an origin of replication functional in *E. coli* and *Agrobacterium*, and a homologous region found in the intermediate vectors pBIOS 308 and pBIOS 309. The presence of this homologous region in the recipient plasmid (pSB1) and the intermediate plasmids (pBIOS 308 and PBIOS 309) is responsible for the phenomenon of homologous recombination.

The intermediate vectors pBIOS 308 and pBIOS 309 are introduced into the *Agrobacterium tumefaciens* cells containing the vector pSB1 by electroporation using the GIBCO BRL CELL PORATOR Voltage Booster according to the method described by Mattanovitch et al. (1989) and the protocol provided by the supplier (Life Technologies, USA).

The agrobacteria containing the superbinary vectors are selected on YT $CaCl_2$ medium in the presence of rifampicin and spectinomycin at a concentration of 50 mg/l. The rifampicin resistance gene is carried out by the bacterial chromosome. The spectinomycin resistance, carried by the plasmids pBIOS 308 and pBIOS 309 (origin of replication in *E. coli*), may be expressed only after homologous recombination with the vector pSB1 (origin of replication functional in *Agrobacterium* and *E. coli*).

The superbinary plasmids obtained after recombination are named pRec 308 (PBIOS 308×pSB1) and pRec 309 (pBIOS 309×pSB1). They possess origins of replication which are functional both in *E. coli* and in *Agrobacterium tumefaciens*, the tetracyclin resistant and the spectinomycin resistant genes, the T-DNA in which are located the cassettes of expression of the Bar and Asr1 (sense or antisense cDNA) genes, and the virB and virG virulence genes of the plasmid pTiBo542.

Characterization of the Superbinary Vectors pRec 308 and pRec 309

These superbinary plasmids pRec 308 (Asr1 gene in the sense direction) and pRec 309 (Asr1 gene in the antisense direction) are characterized by enzymatic restriction with SalI. Southern blotting analysis of the SalI restriction fragments is then carried out with the Bar probe and the Asr1 gene probe (this probe corresponds to the 795 bp EcoRI/XhoI fragment of the vector pHHU516, therefore to the complete cDNA). The profiles obtained are those expected.

Example 4

Maize Plant Transformation

The maize plant transformation is carried out according to the protocol of Ishida et al. (1996).

The transformation begins with a co-culture in which the immature embryos of the maize plants (size ranging from 1 to 1.2 mm) are brought into contact, for 5 minutes, with *Agrobacterium tumefaciens* LBA 4404 containing the superbinary vectors pRec 308 or pRec 309. The embryos are then placed on LSAs medium for 3 days in the dark and at 25° C.

The following step is that of the first selection of the transformed calluses: the "embryo-calluses" are transferred onto LSD 5 medium containing phosphinotricine at 5 mg/l and cefotaxime at 250 mg/l (elimination of *Agrobacterium tumefaciens*). This step is carried out 2 weeks in the dark and at 25° C.

The second selection step is carried out by transferring the embryos which have developed on LSD 5 medium onto LSD 10 medium (phosphinotricine at 10 mg/l) in the presence of cefotaxime, for 3 weeks under the same conditions as in the first selection (25° C., in the dark).

The third selection step consists in excising the type I calluses (fragments of 1 to 2 mm) and in transferring them into the dark for 3 weeks at 25° C. on LSD 10 medium in the presence of cefotaxime.

The regeneration of the plantlets is then carried out by excising the type I calluses which have proliferated and transferring them onto LSZ medium in the presence of phosphinotricine at 5 mg/l and cefotaxime, for two weeks at 22° C. and under continuous light. The plantlets which have regenerated are transferred onto rooting medium (Ishida et al., 1996) for two weeks at 22° C. and under continuous illumination for the development step.

The plants obtained are then transferred to the phytotron for the purpose of acclimatizing them.

Example 5

Demonstration of Expression of the ZMASR1 Protein in the Transformed Plants

The proteins of the leaf samples originating from the transformed plants were extracted according to the method of Damerval et al. (1986), and were analyzed by two-dimensional electrophoresis (TDE) according to the protocol of Riccardi et al. (1998).

Two-dimensional electrophoresis consists in separating polypeptides as a function of their isoelectric point and as a function of their molecular weight (electrophoresis in the presence of SDS). Before electrophoresis, the proteins are extracted and kept under denaturing conditions: the quaternary structure is eliminated. The various polypeptides making up the oligomeric proteins migrate independently during the two electrophoreses. The gels are then stained with silver nitrate.

The two-dimensional gel thus obtained is compared with that produced using proteins of nontransformed A188 plant leaves.

The results obtained from the plants transformed with the coding sequence placed in the "sense" direction show, by simple visual examination of these two gels, stronger expression of the ASR1 protein in the transformed plants compared to the A188 control plants.

The ASR spot observed on the plants transformed with the antisense construct appear to be still detectable, but less strongly, which shows that the "antisense" transformants express the protein less than the control plants.

This protein analysis therefore demonstrates expression of the ASR1 protein in the transformed plants, in an amount which is modified compared to the nontransformed plants.

Example 6

Measurement of the Tolerance to Water Stress of the Transgenic Plants Obtained According to the Invention The resistance to water stress of the transformed plants according to the invention, compared with the control plants, can be assessed using various phenotypic, physiological and/or biochemical analytical methods, for particular irrigation conditions under normal conditions (conventional culture with watering) and under conditions of water stress.

By way of example, the water conditions in the field may be as follows:

normal irrigation in the irrigated part on the basis of 5 mm per day controlled by tensiometers placed 30, 50 and 70 cm deep;

restrictive irrigation, with no supply of water, if possible, until 10 days after flowering. At this approximate date, it is decided to provide water when the stress is judged to be too intense; the rhythm of supply should not exceed 3 mm per day.

The meteorological data and the irrigation conditions are recorded.

The grading carried out at the various periods of flowering and of harvesting consist in measuring:

a) Measurement of the Tolerance to Stress by Phenotypic Observation

The genetic analyses carried out beforehand suggested a potential role for ASR1 in foliar senescence and protandry (time difference between male and female flowering) under conditions of drought. These characteristics are therefore preferentially studied.

Foliar senescence can be studied with morphological measurements which consist in counting the number of dried up leaves and green leaves at 4 dates 15 days apart, from the date of flowering, or at various stages of development. When very different behaviors are observed concerning the rolling up and the color of the leaves, an assessment is made according to a scale of 0 to 5 (from the most tolerant to the least tolerant to stress).

Senescence can also be measured by assaying chlorophyll on samples of foliar disks from the ear leaf at flowering.

Protandry, or time difference between the dates of flowering of the male plants (presence of pollen) and female plants (bristles coming out) is measured as follows: the dates of appearance of the bristles and of the pollen are noted individually for each plant, and the dynamics are represented on a curve of percentage of plants having flowered as a function of time.

Moreover, various assessments were carried out at harvest in order to evaluate the effect of the tolerance to stress on grain production, in particular: the percentage fertilization (ratio of the number of grains per ear/number of fertilizable ovules), the number of rows per ear, the number of grains per row, the water content of the grains, the weight of 1000 grains and the number of fusarium infected plants.

The use of a nondestructive identification test using basta makes it possible to easily distinguish the plants which are resistant to basta from the sensitive plants, in each transgenic descendance, the resistant plants containing the Asr gene genetically linked to the selectable marker gene, unless there has been a recombination event. This test consists in swabbing the end of a leaf with a solution of basta and observing the resulting phenotype, without the vitality of the whole plant being threatened: the end of the leaf undergoes necrosis and dries out when the plant is sensitive, or remains green if the plant is resistant. This makes it possible to observe, on the measurements of tolerance to stress, whether the ASR transgene positively influences the response to stress as a function of expression of the gene in the sense direction or in the antisense direction.

b) Evaluation of the Stress Experienced by the Plants

Samples are taken from the leaves, in order to measure the ABA content (method of Quarrie et al., 1988) and, where appropriate, the expression of the protein by two-dimensional electrophoresis.

The stress experienced by the plants can be evaluated by measuring the basic water potential using a portable pressure chamber on nontransformed plants, under control conditions and under conditions of water stress. Measurements of the relative water content of the leaves can also be made.

Foliar senescence, which permits a decrease in the surface of evaporation, and re-mobilization of metabolites to the remainder of the plant, was measured as described above, on adult plants after flowering, by counting the number of leaves of which at least 50% of the surface is dry.

Figure 4:
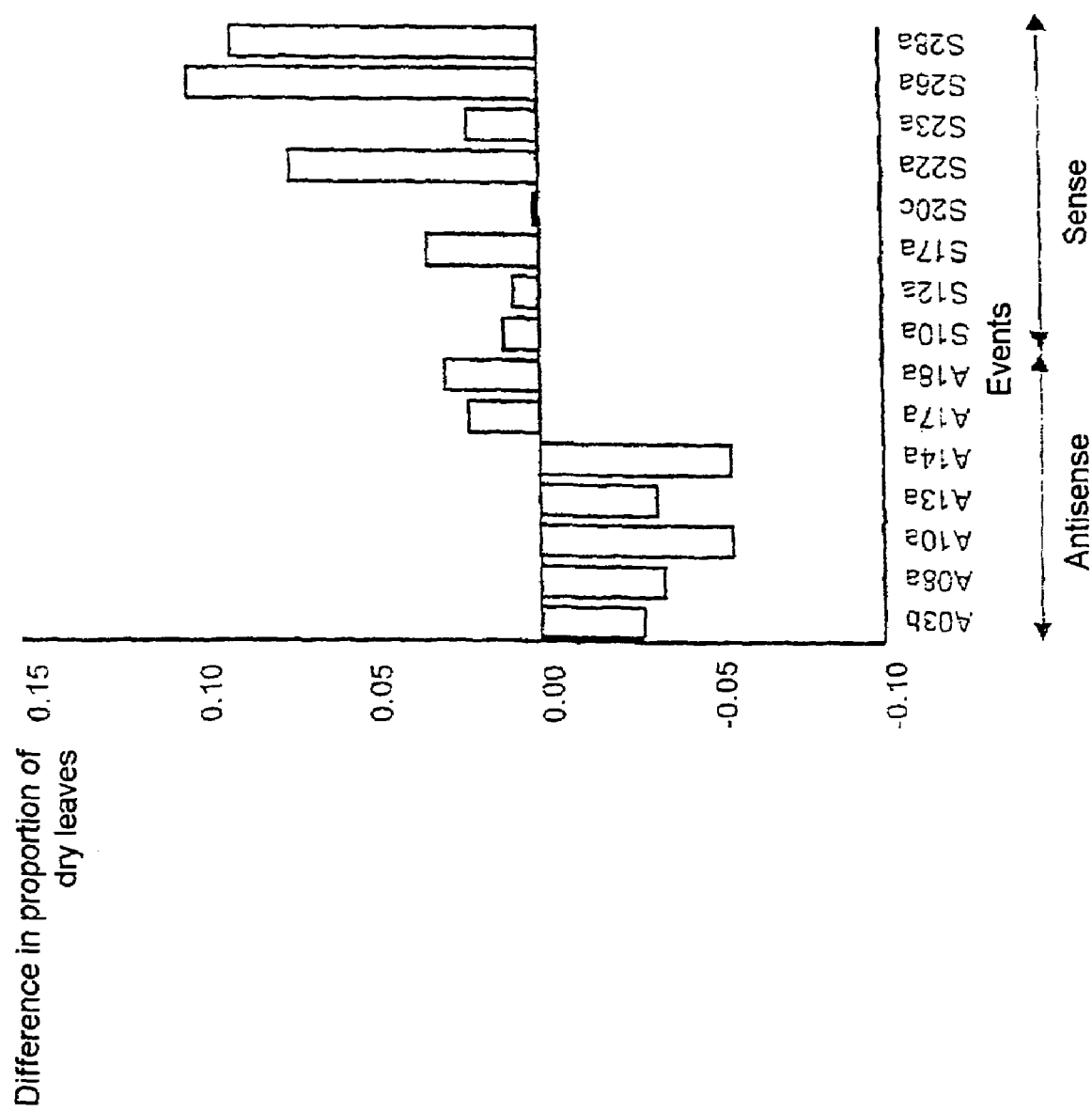
FIG. 4 represents the effect of each "antisense" or "sense" transformation event, relative to its own control (Basta sensitive), on foliar senescence, the effect being measured on the first day of grading after flowering.

A significant effect of expression of the ASR protein on the proportion of dry leaves is observed. In fact, when related to their own controls, the "sense" events show, at a given time, a greater proportion of dry leaves than "antisense" events (FIG. 4). Similarly, under conditions of water stress, the foliar senescence kinetics measurements show that the "sense" events become senescent more rapidly than the "nontransformed" and that the "antisense" events become senescent less rapidly than the "nontransformed" (FIG. 5).

The term "sense" event is intended to mean an event derived from an initial step of transformation with an expression cassette containing the ASR sequence placed in the sense direction. The term "antisense" event is intended to mean an event derived from an initial step of transformation with a cassette containing the ASR sequence placed in the antisense direction.

The "sense" events, which become senescent more rapidly than the "nontransformed" under conditions of water stress, therefore exhibit a selective advantage of tolerance to water stress, in particular in the case of a stress of long duration (decrease in the surface of evaporation and re-mobilization of metabolites to the remainder of the plant).

The "antisense" events, which become senescent less rapidly than the "nontransformed" under conditions of water stress, also exhibit an advantage, in particular in the case of a water deficit of short duration. In fact, these plants will have maintained a greater surface of evaporation and will therefore benefit more fully from a subsequent supply of water (rain or irrigation).

In addition, the measurements of the stress experienced by the plants (ABA content in leaves) revealed a slight but highly significant stress: respectively 616 and 512 ng ABA/g solids in the stressed and control plants, i.e. an increase of approximately 100 ng of ABA per gram of solids in the stressed plants. This response is the same for the "sense" and "antisense" events, and also for the nontransformed plants. The transformation does not therefore appear to have an effect on the accumulation of ABA in the leaves.

These results therefore confirm that, in the presence of a slight water stress and of low ASR expression in the transformed plants, significant differences are already observed.

Moreover, the effect of the tolerance to water stress on grain production was measured relative to the yield of grain, the weight of one thousand grains and the number of ears per plant. The results obtained with a low water stress show grain yield measurements comparable between transformed ("sense" and "antisense") plants and nontransformed plants, taken under conditions of stress or under normal conditions.

The transformation, firstly, and the tolerance to water stress, secondly, do not therefore appear to affect the grain yield of the plants.

Plant growth measurements were also taken. The lengths of 3 leaves above and below the ear were measured on "sense" and "antisense" plants after flowering, in the absence of water stress. A highly significant difference was observed for the 3 leaves:

for the leaves
   F0, antisense=78.41 cm ($p<0.01$)
      sense=76.11 cm
   F1, antisense=77.96 cm ($p<0.01$)
      sense=75.76 cm
   F2, antisense=75.04 cm ($p<0.01$)
      sense=72.94 cm Overall, a significant difference of 2 cm in length is therefore observed for these 3 leaves, the leaves of the "sense" plants being smaller than those of the "antisense" plants. This decrease in leaf growth observed in the "sense" events therefore correlates with a greater senescence, the two phenomena resulting in a decreased surface of evaporation, which allows the plant to more successfully tolerate water stress.

BIBLIOGRAPHY

An et al. (1986), Plant Physiol. 81: 86–91
Altschul et al. (1990), J. Mol. Biol. 215: 403–410
Anderson O. D. et al., (1989), T.A.G., 77: 689–700
Bechtold et al. (1993), Comptes rendus Académie des Sciences Paris Serie 3, 316: 1194–1199
Canel C. et al. (1995), Plant Physiol. 108 (1995), 1323–1325
Chupeau et al. (1989), Biotechnology, 7(5): 503–508
Church and Gilbert, (1984) Proc. Natl. Acad. Sci. USA, 81: 1991–1995
Damerval et al. Electrophoresis 7: 52–54, 1986
Depicker et al., (1982), J. Mol. Appl. Genet., 1, 561–573
Depigny-This et al., (1992), Plant Mol. Biol., 20: 467–479
De Vienne et al., (1999), Journal of Experimental Botany, 50 (332): 303–309
Finer et al. (1992), Plant Cell Report, 11: 323–328
Franck et al. (1980), Cell 21: 285–294
Fromm M. et al. (1990), Biotechnology, 8: 833–839
Guerche et al. (1987), Mol. Gen. Genet., 206: 382
Herrera-Estrella et al. (1983), EMBO J. 2, 987–995
Hiei et al. (1994), The Plant Journal, 6, 271–282
Hoekema et al. (1983), Nature, 303, 179–180
Iusem et al., (1993), Plant Physiol., 102: 1353–1354
Ishida et al. (1996), Nature Biotechnology 14: 754–750
Kasuga et al. (1999), Nature Biotechnology, 17: 287–291
Kay et al., (1987) Science, 236: 4805

Mattanovitch et al., (1989), Nucleic Acids Research, 17(16): 6747

Mc Elroy et al. (1991), Molecular and General Genetics, 231(1), 150–160

Neuhaus et al. (1987), Theoretical and applied Genet., 75(1): 30–36

Quarrie et al. (1988), Planta 173: 330–339

Riccardi et al. (1998), Plant Physiol., 117: 1253–1263

Sambrook et al. (1989), Molecular cloning, A laboratory manual, 2nd Edition, Cold Spring Harbour Laboratory Press Schocher et al. (1986), Biotechnology 4: 1093–1096

Silhavy D. et al. (19–95), Plant Mol. Biol. 27 (1995), 587–595

Thomas et al. (1999), Plant Science 140, 21–30

Watson et al. (1994), ADN recombinant [Recombinant DNA], Ed. De Boeck University pp 273–292

Zambryski et al. (1989) Cell, 56, 193–201

Zeewart and Creelman (1988), Annu. Rev. Plant Physiol. Plant Mol. Biol. 39: 439–473

The invention claimed is:

1. A method for obtaining a transformed plant exhibiting an increased amount of ASR (ABA-water stress-ripening-induced) protein, conferring on said plant increased resistance to water deficit stress compared to a non-transformed plant, comprising transforming at least one plant cell with a vector containing an expression cassette comprising a nucleotide sequence encoding an ASR protein, wherein said ASR protein comprises the amino acid sequence of SEQ ID NO: 2; and culturing the cell thus transformed so as to generate a plant containing, in its genome, said expression cassette, and wherein said plant expresses said protein.

2. The method according to claim 1, wherein said nucleotide sequence encoding said ASR protein comprises sequence SEQ ID No 1.

3. The method according to claim 1, wherein the expression cassette comprises a promoter for constitutive expression of the nucleotide sequence encoding the ASR protein.

4. A plant, or plant part comprising a nucleotide sequence encoding the amino acid sequence of SEQ ID NO: 2, wherein said plant or plant part is obtained by the method of claim 1.

5. The plant, or part of a plant, according to claim 4, that exhibits an increase in expression of the ASR protein compared to a non-transformed plant.

6. The plant, or part of a plant, according to claim 4, which is a field crop plant selected from maize, wheat, rapeseed, sunflower and peas.

7. The plant, or part of a plant, according to claim 4, which is maize.

8. The method according to claim 3, wherein said promoter is a rice actin promoter operably linked to a rice actin gene intron.

* * * * *